(12) United States Patent
Chi et al.

(10) Patent No.: US 7,296,361 B2
(45) Date of Patent: Nov. 20, 2007

(54) MEASURING DEVICE AND METHOD OF MEASURING

(75) Inventors: David H. Chi, Pittsburgh, PA (US); Michael Rhodes Lovell, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/903,718

(22) Filed: Jul. 30, 2004

(65) Prior Publication Data

US 2005/0115093 A1 Jun. 2, 2005

Related U.S. Application Data

(60) Provisional application No. 60/491,361, filed on Jul. 31, 2003.

(51) Int. Cl.
 *A61B 5/103* (2006.01)
 *A61B 5/107* (2006.01)
 *G01B 1/00* (2006.01)
 *G01B 5/20* (2006.01)

(52) U.S. Cl. .................. 33/512; 33/511; 33/542; 600/587

(58) Field of Classification Search .......... 33/511–512, 33/542, 544, 544.2, 558.01, 558.04, 558.2, 33/558.4; 600/587–591, 595; 606/102, 606/107, 88, 167, 198, 205
See application file for complete search history.

(56) References Cited

U.S. PATENT DOCUMENTS

| | | | | |
|---|---|---|---|---|
| 4,226,025 A * | 10/1980 | Wheeler | .................. | 33/512 |
| 4,685,474 A * | 8/1987 | Kurz et al. | .................. | 600/591 |
| 4,791,940 A * | 12/1988 | Hirschfeld et al. | ......... | 600/589 |
| 4,845,646 A * | 7/1989 | Marquis et al. | ............... | 33/504 |
| 5,156,161 A * | 10/1992 | Lollar | ........................ | 600/587 |
| 5,249,366 A * | 10/1993 | Takahashi et al. | ............ | 33/512 |
| 5,317,814 A * | 6/1994 | Rogler | ........................ | 33/542 |
| 5,376,093 A * | 12/1994 | Newman | ...................... | 606/88 |
| 5,484,447 A * | 1/1996 | Waldock et al. | ............ | 606/107 |
| 6,026,351 A * | 2/2000 | Takeuchi | ...................... | 33/503 |
| 6,110,200 A * | 8/2000 | Hinnenkamp | ................ | 33/512 |
| 6,223,136 B1 * | 4/2001 | Geiger | ......................... | 33/1 L |
| 6,276,956 B1 * | 8/2001 | Cook | ........................ | 33/27.02 |
| 6,301,799 B1 * | 10/2001 | Ho | .............................. | 33/807 |
| 6,574,582 B1 * | 6/2003 | Geiger | ......................... | 33/1 L |
| 6,820,347 B2 * | 11/2004 | Mellander | .................. | 33/555.1 |
| 2003/0047009 A1* | 3/2003 | Webb | .......................... | 33/512 |

* cited by examiner

Primary Examiner—Yaritza Guadalupe-McCall
(74) Attorney, Agent, or Firm—Bartony & Hare, LLP

(57) ABSTRACT a device for measuring dimensions in a hollow organ of the body, includes: a length of conduit; a measuring mechanism on one end of the conduit; and an indicator in connection with a second end of the conduit. The indicator is in operative connection with the measuring mechanism to provide an indication of a dimension measured by the measuring mechanism. In one embodiment, the measuring mechanism includes extending members that open and close in the manner of forceps to contact the walls of the organ.

23 Claims, 4 Drawing Sheets

MEASURING DEVICE AND METHOD OF MEASURING

CROSS REFERENCE TO RELATED APPLICATION

This application claims the benefit of U.S. Provisional Patent Application Ser. No. 60/491,361, filed Jul. 31, 2003, the disclosure of which is incorporated herein by reference.

FIELD OF THE INVENTION

The present invention relates to measuring devices and to methods of measuring, and, particularly, to measuring devices for measuring dimension in hollow organs of the body (especially airways) and to methods of measuring such dimensions.

BACKGROUND OF THE INVENTION

Infants can be born with or develop narrowing of the trachea or larynx for a variety of medical ailments. The present method of evaluating the amount of narrowing in these areas is limited. The current technique involves passing various endotracheal tubes of known diameter into the stenotic region. After a tube passes though the narrowing, an airleak is assessed, and the percent stenosis is approximated as the diameter of the tube relative to the age appropriate lumen. This technique assumes that the stricture is concentric and relies on surgeon's insertion method. Not only is the present method potentially inaccurate, but it may be traumatic to the tissue in the stenotic region.

SUMMARY OF THE INVENTION

In one aspect, the present invention provides a device for measuring dimensions in a hollow organ of the body, including: a length of conduit; a measuring mechanism on one end of the conduit; and an indicator in connection with a second end of the conduit. The indicator is in operative connection with the measuring mechanism to provide an indication of a dimension measured by the measuring mechanism. In one embodiment, the measuring mechanism includes extending members that open and close in the manner of forceps to contact the walls of the organ. The user of the device can, for example, be provided with tactile, visual and/or other indications that the extending members have contacted the wall(s) of the organ to be measured. The indicator preferably includes an indicating element that is calibrated to the distance between the distal ends of the extending members. The indicating element can, for example, move to provide the user of the device with an indication of the distance between the distal ends of the extending members. The indicating element can also or alternatively be in operative connection with a display to provide the user of the device with a displayed indication of the distance between the distal ends of the extending members.

The conduit of the measuring device can be flexible or be rigid, but should be suitable to transport the measuring mechanism thereon to the internal area to be measured. In one embodiment, the conduit is adapted for insertion into an airway. The conduit can, for example, be an extending (or insertion) section or member of an endoscope. In that embodiment, the extending members of the measuring device are, for example, connected to a forceps-like handle of the endoscope via a connecting member passing through the extending section of the endoscope to control the distance between the distal ends of the extending members. The device can further include a port for a camera or other viewing device on the second end of the conduit to enable visualization of the area to be measured or the action of the measuring mechanism. Endoscopes, for example, are commonly provided with such a camera, video or viewing port.

The present invention also provides a method of measuring dimensions in a hollow organ of the body, comprising the steps: inserting a conduit into a hollow organ, the conduit having a measuring mechanism on the end thereof that is inserted into the organ, the conduit having in connection with the other end thereof an indicator in operative connection with the measuring mechanism to provided an indication of a dimension measured by the measuring mechanism to a user.

As described above, the measuring mechanism can include extending members that open and close in the manner of forceps. As also described above, the conduit can be an extending or insertion section of an endoscope. In one embodiment, the conduit is inserted into an airway to measure a narrowing therein. The user can measure the width or dimension of such narrowings in multiple planes (for example, by rotating the device and taking multiple measurement in distinct orientations) to get an accurate representation of the dimensions of the narrowing.

DESCRIPTION

In an effort to increase the accuracy of measurements of, for example, trachea narrowing, the present invention provides an instrument or device that can, for example, be readily incorporated into an existing endoscope 10 (see FIGS. 1 and 2) through relatively minor retrofitting thereof. In one embodiment, a measuring device of the present invention is passed through a bronchoscope to accurately assess the size of the trachea or larynx using, for example, a measuring mechanism on the forward end of the measuring device.

Figure 3:
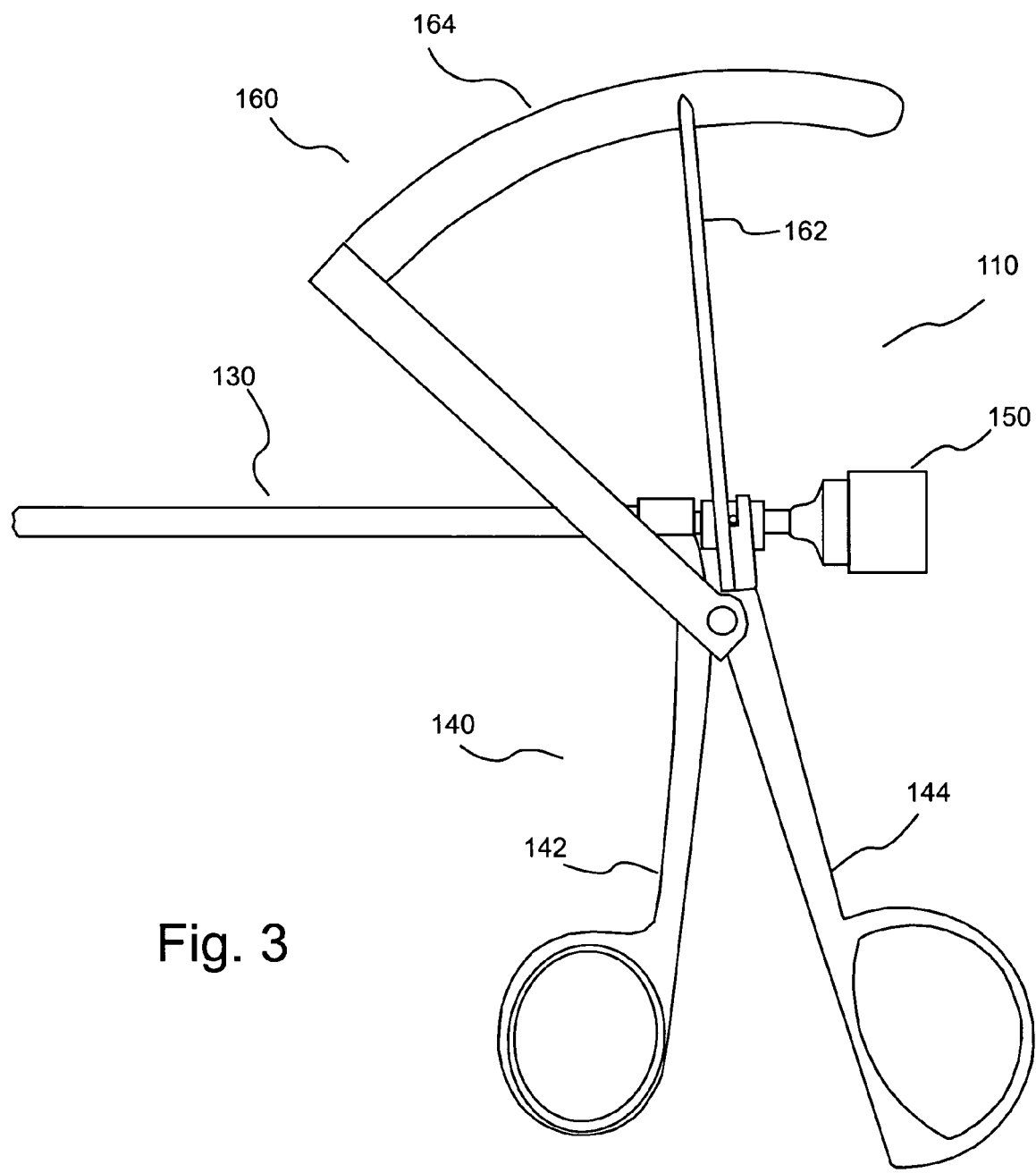
FIG. 3 illustrates one embodiment of a measuring device of the present invention including a mechanical indicator.
Figure 4:
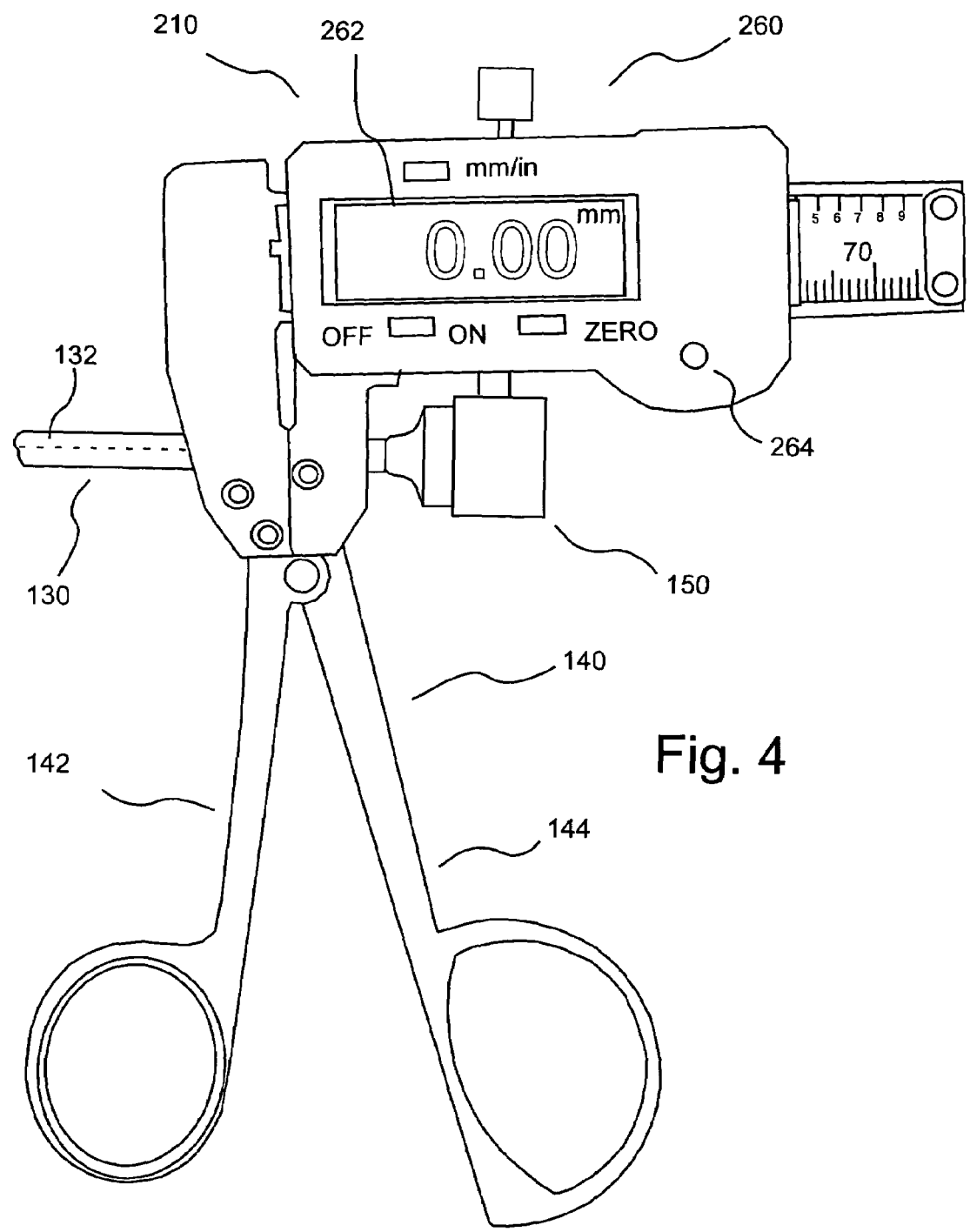
FIG. 4 illustrates another embodiment of a measuring device of the present invention including a digital indicator.

Two different measuring devices 110 and 210 of the present invention (illustrated in FIGS. 3 and 4, respectively) were assembled and tested in several studies of the present invention. In the embodiment of FIG. 3, a mechanical caliper 160 was attached to the handle of an endoscope to measure the airway. In the embodiment of FIG. 4, a digital caliper system 260 provides an electronic measurement of the amount of narrowing.

Figure 1:
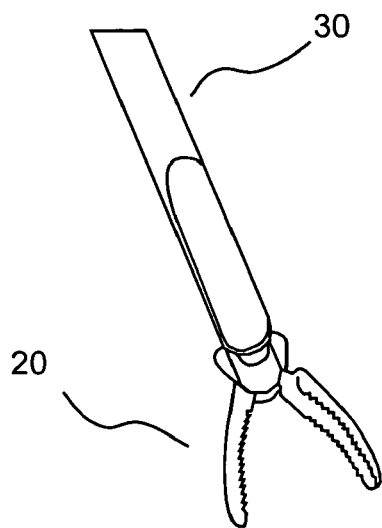
FIG. 1 illustrates a forward end of one currently available endoscope equipped with gripping or grabbing forceps on the forward end of the extending or insertion member of the endoscope.
Figure 2:
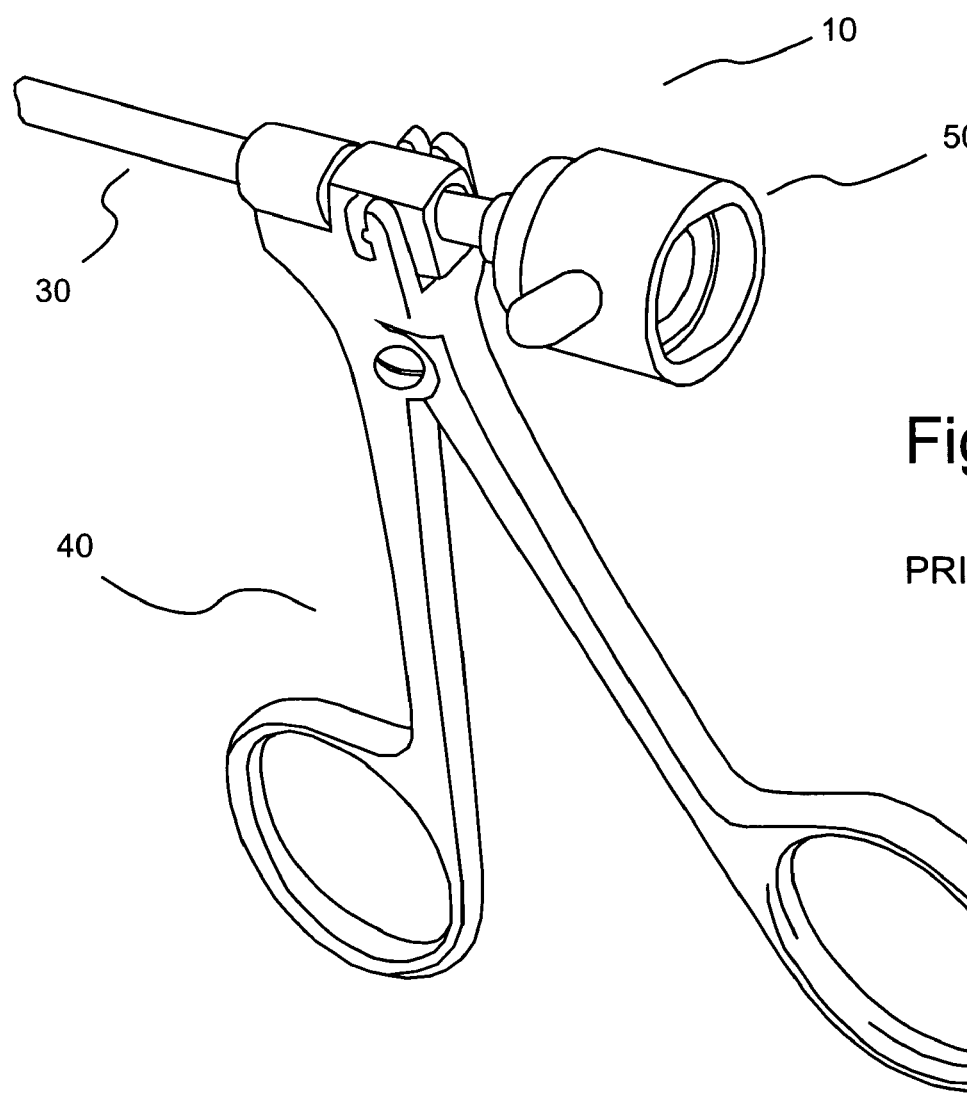
FIG. 2 illustrates a rearward end of the endoscope of FIG. 1 showing a forceps-like or scissor-like handle thereof for control of the forceps on the forward end of the insertion member or tube.

Endoscopes are devices that are utilized by medical professionals to perform minimally invasive treatments on patients. In its most basic form, an endoscope (see FIGS. 1 and 2) is a tool that is used to visualize the interior of a hollow organ or to grab small objects or body materials when equipped with gripping forceps on the distal end thereof. For example, an endoscope can be used to remove unwanted material in blocked passages such as airways or nostrils. As shown in FIGS. 1 and 2, in one embodiment endoscope 10 includes two basic mechanical parts: forceps 20 (see FIG. 2) at an end of an extending member 30 and control handles 40. The primary action in endoscope 10 occurs when handles 40 are opened and closed. In that regard, forceps 20 are mechanically coupled to handles 40. Endoscope 10 also includes a camera mount or port 50 on the handle end so that a physician can view a video representation of the action of forceps 20.

Figure 5:
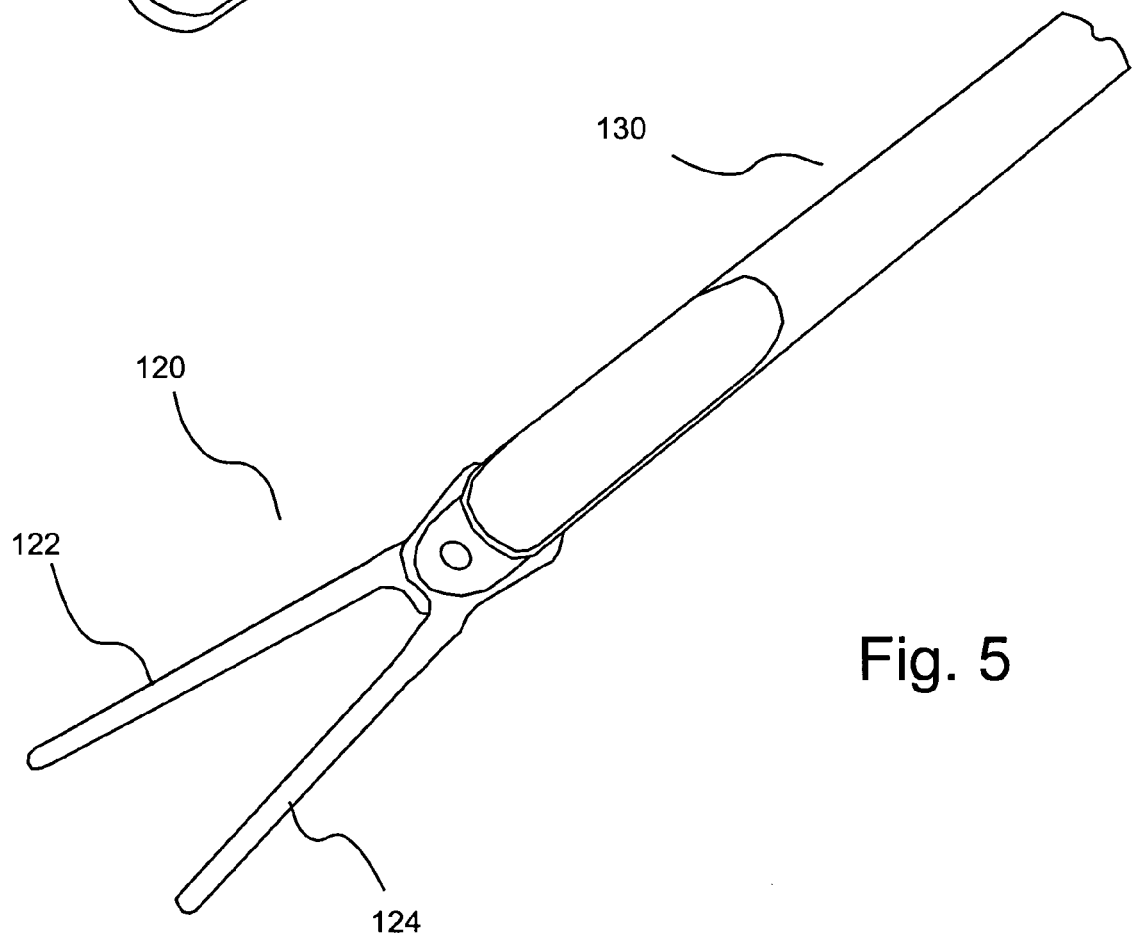
FIG. 5 illustrates one embodiment of a measuring mechanism used in the embodiments of FIGS. 3 and 4 of the present invention including extending members having a forceps-like opening and closing motion.

In the case of measuring devices 110 and 210 of the present invention, the grasping or grabbing forceps of a commercially available endoscope (available from Karl Storz GmbH & Co. KG of Tuttlingen, Germany) were removed and a measuring device or mechanism 120 was attached to the end of extending or insertion member 130 of endoscopic measuring device 110. Measuring mechanism 120 includes extending members 122 and 124 having a forceps- or scissor-like opening and closing motion as shown, for example, in FIGS. 5 and 6. Referring to FIG. 3, a mechanical/analog indicating or display device 160 similar in operation to a protractor can, for example, be mounted on a handle 140 and appropriately calibrated using methods known in the mechanical arts so that there is a direct correlation between the indicated measurement and the opening of handle members 142 and 144 of handle 140 (and thereby the distance between the tips of the extending members 122 and 124). Measuring devices other than calipers can also be used in the present invention. Such measuring devices can, for example, be mechanical (such as expanding rings that take the form of the narrowing) or use energy such as sound or light to measure the narrowing.

The devices and methods of the present invention enable ear, nose and throat (ENT) surgeons to perform relatively non-invasive measuring techniques to measure narrowing in the trachea or larynx and even other areas of the body. Once again, the currently practiced measuring technique is inadequate as it can be traumatic to the vocal cords, trachea, and larynx. Moreover, the present method does not consider bulges in the throat—it assumes that the airway is constricted concentrically. Unlike the currently practiced method, the devices and measurement procedures of the present invention are relatively non-invasive. In that regard, the calipers/extending members will not be intrusive to the patient. Moreover, the devices of the present invention are also practical and allow accurate, repeatable readings without intruding on a surgeon's ability to manipulate the endoscope.

In the embodiments of FIGS. 3 and 4, measuring device 120 was operatively connected to the end linkages each of mechanical caliper 160 (see FIG. 3) and a digital caliper 260 (see FIG. 4). As discussed above, the airway measuring systems or devices of the present invention preferably provide repeatable and accurate results while not harming the patient in any way. Therefore, in the embodiments of FIGS. 3 through 6, forceps-like extending members 122 and 124 were made straight to allow for linear calibration with motion of handles 142 and 144. Moreover, the tips of extending members 122 and 124 were blunted so that they would not pierce the tissue in the stenotic region. Extending members 122 and 124 were also made of a length to accommodate the 1.2 cm maximum airway opening of an infant. Other size forceps may be used with adults or for use in measurements in other areas of the body. With forceps-like extending members 122 and 124 of the present invention, an airway can be measured in a single step, thus making the procedure safer and faster than original technique. Forceps-like extending members 122 and 124 of the present invention generally cause the endoscope to loose its grasping function. To obtain the measurement of a narrowing in multiple planes, the user can rotate extending member 122 and 124 of measurement device 120 through, for example, the lateral and anterior-posterior orientation, while taking multiple measurements to get a more accurate representation of the narrowing. No longer must the surgeon assume that the narrowing is concentric.

As shown in FIGS. 3 and 4, both of the illustrated measurement devices are directly attached using the existing handle pivot screw assembly of a currently available endoscope. As illustrated in FIG. 3, mechanical caliper 160 includes a pointer 162 used in connection with a "measuring arc" 164 that indicates the size of the larynx/trachea using, for example, the angle of movement of handles 142 and 144. Mechanical airway caliper 160 was easily calibrated using known diameter tubes so that an indicator or indicators could be placed in operative connection with measuring arc 164 to provide a visual indication of the narrowing distance. The resolution of one early embodiment of the manual caliper (which was not optimized) was approximately 1 mm, which is significantly more accurate than the currently practiced tube insertion technique of measuring narrowing distance. Mechanical caliper 160 can be readily made to be symmetric and can thus be used with either the right or left hand.

Figure 6:
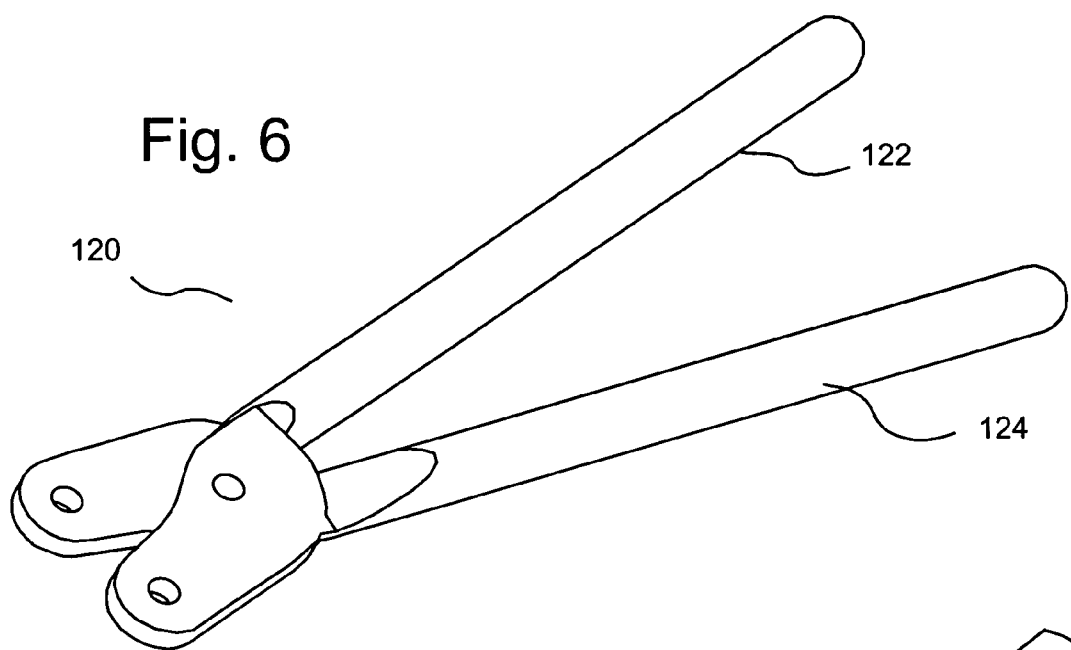
FIG. 6 illustrates the extending members of FIG. 5 operatively attached to the end of an insertion member of an endoscope.

In the embodiment of FIG. 4, digital caliper 260 measures the linear distance traveled by a rigid member such as a rod that operatively connects extending member 122 and 124 to handles 142 and 144 in endoscopic measuring device 210. In the case of measuring device 210, an off-the-shelf digital measuring device 260 (available, for example, from Woodcutters Supply Inc.) was secured to handles 142 and 144 to be linearly slideable with the motion of the rod. A digital caliper or other measuring device can provide several advantages over mechanical measuring devices. For example, one advantage is accuracy—digital measuring device 260 and other digital measuring devices can, for example, measure to an accuracy of 0.1 mm. In addition, digital measuring device 260 provides an exact reading of the narrowing upon a display 262 rather than relying on the health professional's ability to read the value from an arc-pointer or other mechanical indicating system. Finally, a digital system can be more readily equipped to provide digital recording/storage of several measurements of the airway profile that can be directly downloaded and saved onto, for example, a PC in digital format. In that regard, digital measuring device 260 of FIG. 6 includes a data port 264 that attaches to a PC via an appropriate data cable as known in the art. Alternatively, digital measuring device can be equipped with a wireless transmission system for transfer of data. In the embodiment of FIG. 6 (and as with many existing hand-held calipers), digital display 262 is optimized for viewing by right-handed users.

In the embodiment of measuring devices 110 and 210, the ends of handles 142 and 144 can, for example, be connected (for example, pinned) to the first end of a connecting member (represented by dashed line 132 in FIG. 4) such as a wire, a rod or other rigid member that was positioned within the hollow shaft of extending member 130. The end of handles 142 and 144 can be connected to connecting member 132 so that when the handles 142 and 144 are opened, connecting member 132 moves toward handles 142 and 144. Likewise, when handles 142 and 144 are closed, connecting member 132 moves away from handles 142 and 144. At the second end of connecting member 142, extending members 122 and 124 can be connected (for example, pinned) such that they open (that is, the distal ends spread apart) when connecting member 132 moves toward handles 142 and 144 (that is, when handles 142 and 144 are opened) and close when connecting member 132 moves away from handles 142 and 142 (that is, when handles 142 and 144 are closed). For a known extending member geometry, the distance between the ends of the extending member can, for example, be directly determined by measuring the linear motion of connecting member 132. As described above, either digital or mechanical indicating elements or devices can be used to accurately measure the linear motion of connecting member 132.

The foregoing description and accompanying drawings set forth preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A device for measuring dimensions in a hollow organ of the body, comprising:
   a length of conduit;
   a measuring mechanism on one end of the conduit;
   an indicator in connection with a second end of the conduit, the indicator being in operative connection with the measuring mechanism via a connector extending through the length of conduit and translating information of motion of the measuring mechanism to the indicator to provide an indication of a dimension measured by the measuring mechanism to a user of the device; and
   a port for a viewing device on of the conduit to operatively connect a viewing device adapted to visualize of the area to be measured or the action of the measuring mechanism.

2. The device of claim 1 wherein the measuring mechanism comprises extending members that open and close in the manner of forceps to contact walls of the organ in an area to be measured.

3. The device of claim 2 wherein the indicator includes an indicating element that is calibrated to the distance between the distal ends of the extending members.

4. The device of claim 3 wherein the indicating element moves to provide the user of the device with an indication of the distance between the distal ends of the extending members.

5. The device of claim 3 wherein the indicating element is in operative connection with a display to provide the user of the device with an indication of the distance between the distal ends of the extending members.

6. The device of claim 5 wherein the display is in operative connection with a digital caliper.

7. The device of claim 6 wherein the digital caliper includes a data port for transmission of data.

8. The device of claim 2 wherein the conduit is an extending section of an endoscope, the extending members of the measuring device being connected to a forceps-like handle of the endoscope via the connecting member passing through the extending section of the endoscope to control the distance between the distal ends of the extending members.

9. The device of claim 2 wherein the extending members are generally linear.

10. The device of claim 1 wherein the conduit is flexible.

11. The device of claim 1 wherein the conduit is rigid.

12. The device of claim 1 further comprising a viewing device operable via the port to visualize of the area to be measured or the action of the measuring mechanism.

13. The device of claim 1 wherein the conduit is adapted for insertion into an airway.

14. A method of measuring dimensions in a hollow organ of the body, comprising the steps:
   inserting a conduit into a hollow organ,
   operating a measuring mechanism on an end of the conduit that is inserted into the organ, the conduit having in connection with the other end thereof an indicator in operative connection with the measuring mechanism via a connector extending through the conduit and translating information of motion of the measuring mechanism to the indicator to provide an indication of a dimension measured by the measuring mechanism to a user, and
   operating a viewing device via a port of the conduit during the operation of the measuring mechanism to visualization the area to be measured or the action of the measuring mechanism.

15. The method of claim 14 wherein the measuring mechanism comprises extending members that open and close in the manner of forceps to contact wails of the organ in an area to be measured.

16. The method of claim 15 wherein the indicator includes an indicating element that is calibrated to the distance between the distal ends of the extending members.

17. The method of claim 16 wherein the indicating element moves to provide the user of the device with an indication of the distance between the distal ends of the extending members.

18. The method of claim 17 wherein the indicating element is in operative connection with a display to provide the user of the device with an indication of the distance between the distal ends of the extending members.

19. The method of claim 15 wherein the conduit is an extending section of an endoscope, the extending members of the measuring device being connected to a forceps-like handle of the endoscope via the connecting member passing through the extending section of the endoscope to control the distance between the distal ends of the extending members.

20. The method of claim 14 wherein the conduit is flexible.

21. The method of claim 14 wherein the conduit is rigid.

22. The method of claim 14 wherein the viewing device is a camera.

23. The method of claim 14 wherein the conduit is inserted into an airway to measure a narrowing therein.

* * * * *

UNITED STATES PATENT AND TRADEMARK OFFICE
CERTIFICATE OF CORRECTION

PATENT NO. : 7,296,361 B2 Page 1 of 1
APPLICATION NO. : 10/903718
DATED : November 20, 2007
INVENTOR(S) : David H. Chi and Michael Rhodes Lovell It is certified that error appears in the above-identified patent and that said Letters Patent is hereby corrected as shown below:

Col. 6 Claim 15, line 38, "wails" should be changed to --walls--.

Signed and Sealed this

Fourteenth Day of October, 2008

JON W. DUDAS
*Director of the United States Patent and Trademark Office*